United States Patent [19]

Brink et al.

[11] Patent Number: 5,240,994
[45] Date of Patent: Aug. 31, 1993

[54] SOLID SURFACE COATED WITH A HYDROPHILIC BIOPOLYMER-REPELLENT OUTER LAYER AND METHOD OF MAKING SUCH A SURFACE

[75] Inventors: Carina Brink, Va Frölunda; Eva Osterberg, Kungälv; Krister Holmberg, Molndal, all of Sweden

[73] Assignee: Berol Nobel AB, Stenungsund, Sweden

[21] Appl. No.: 759,019

[22] Filed: Sep. 13, 1991

[30] Foreign Application Priority Data

Oct. 22, 1990 [SE] Sweden ................................ 9003364

[51] Int. Cl.$^5$ .............................................. C08G 69/00
[52] U.S. Cl. ................................... 525/54.2; 525/54.21; 525/54.23; 525/54.26; 525/54.24; 525/54.31; 525/60; 525/57
[58] Field of Search ............... 525/57, 60, 54.2, 54.24, 525/54.26, 54.31, 54.21, 54.23

[56] References Cited

U.S. PATENT DOCUMENTS 4,794,002 12/1988 Henis et al. .................. 424/488

OTHER PUBLICATIONS

Kiss et al., article entitled "Surface grafting of polyethylneneoxide optimized by means of ESCA in Pogr. Colloid & Polymer Sci." 74:113-119 (1987).
Nikita in "The Chemistry of Cellulose and Wood", Ch IV, pp. 62-71 (1966) Jerusalem, S. Monson.

Primary Examiner—John Kight, III
Assistant Examiner—Jeffrey Culpepper Mullis

[57] ABSTRACT

A solid surface having anionic groups capable of reacting with a polyethylene imine substituted at least in part by at least 50% by weight of a hydrophilic nonionic polymer having a molecular weight within the range from about 400 to about 200,000 is provided with a hydrophilic biopolymer-repellent outer surface layer thereof by reacting such a polyethylene imine substituted by nonionic hydrophilic polymer with anionic groups on the solid surface, in an amount sufficient to produce biopolymer-repellent solid surface, and accordingly having low spontaneous adsorption of proteins and other biopolymers through electrostatic attraction and/or hydrophobic interaction.

7 Claims, No Drawings

SOLID SURFACE COATED WITH A HYDROPHILIC BIOPOLYMER-REPELLENT OUTER LAYER AND METHOD OF MAKING SUCH A SURFACE

Biofouling, i.e., the undesired adsorption of proteins and other biopolymers on solid surfaces, is a well-known problem in many biotechnical and medicotechnical contexts. A primary adhesion of soluble polymers to a solid surface frequently causes cells, cell debris, bacteria, virus, etc. to be bonded to the surface, resulting for example in the clogging of membranes for ultra- and microfiltration, impaired performance of chromatographic columns, and bacterial infections in conjunction with the use of catheters.

It is generally assumed that the surface adhesion of cells and lower organisms is preceded by the adsorption of biopolymers, primarily proteins. Thus, by minimising the protein bond to a surface, it should be possible to avoid biofouling.

The problem is encounted with both organic and inorganic surfaces, although it may be more pronounced for some materials than for others. It is postulated that the adsorption of polymers to solid surfaces from aqueous solutions arises from hydrophobic interactions and electrostatic forces of attraction.

One way, and a very interesting one, to prevent biofouling is to coat the surface with a film of a hydrophilic uncharged material. Examples of such materials are polysaccharides, such as dextran, and polyethylene glycol derivatives. To inhibit hydrophobic forces of attraction, the layer should not be think preferably not below 10 nm. Furthermore, in respect of protein repellency the film material should contain side chains having a high mobility and extending into the medium with which the surface is in contact. Polyethylene glycols anchored at one end to a polymer matrix are thus far more effective than polyethylene glycols having both ends bonded to the matrix.

One way of attaching polyethylene glycol side chains to a solid polymer surface is to first subject the surface to acidic etching, then to adsorb a cationic polymer, polyethylene imine, to the surface, and finally to react a reactive polyethylene glycol derivative to available amino groups in the polyethylene imine layer. This technique is described in *Prog. Colloid Polym. Sci.* 74 113-119 (1987). The acidic etching (which is carried out in a potassium permanganate solution in concentrated sulphuric acid), results in the formation of carboxylic acid and sulphonic acid groups as well as sulphuric acid ester groups on the surface. To this highly negatively charged polymer surface, the cationic polyethylene imine is extremely strongly bonded by electrostatic forces. Besides, it is likely that salt formations between ammonium groups in the polyethylene imine and carboxylated sulphonate groups on the surface are gradually transformed into amide or imide bonds upon drying, whereby an even more stable anchoring of the polyethylene imine to the surface is obtained.

Even though hydrophilic surfaces produced by the technique described in the above paper give an improved repellency of biopolymers, the adsorption thereof is still unacceptably high for most applications.

According to the present invention, it has now proved possible to obtain an even denser grafting of hydrophilic polymer chains to the solid surface than is obtainable with the method previously described in which polyethylene glycol is bonded to a surface made amino-functional by adsorption of polyethylene imine. As a consequence of the more efficient grafting to the surface of hydrophilic polymer chains, the method of the present invention imparts a far better protein repellency to the surface, so that biofouling is effectively prevented.

In the process according to the invention, a solid surface is provided with a hydrophilic outer layer of hydrophilic polymer by reacting the solid surface comprising anionic groups capable of reacting with ammonium groups with a polyethylene imine having at least 50% by weight hydrophilic nonionic polymer groups attached to amino groups thereof. Preferably, the polymer has such a molecular weight and is present in such amount that the hydrophilic outer layer has a thickness of at least 100 Å.

The invention thus provides a process for preparing a biopolymer-repellent solid surface having low spontaneous adsorption of proteins and other biopolymers through electrostatic attraction and/or hydrophobic interaction and useful in biochemical applications, comprising reacting a solid surface having anionic groups capable of reacting with ammonium groups, with polyethylene imine substituted at least in part by at least 50% by weight of nonionic hydrophilic polymer thereby linking the polyethylene imine/hydrophilic polymer to the surface via anionic groups thereof, and forming a hydrophilic outer surface layer repellent to biopolymer and having low spontaneous adsorption of proteins and other biopolymers through electrostatic attraction and/or hydrophobic interaction.

The invention further provides a biopolymer-repellent solid surface useful in biochemical applications, and having low spontaneous adsorption of proteins and other biopolymers through electrostatic attraction and/or hydrophobic interaction, the solid surface having a hydrophilic outer surface layer comprising polyethylene imine which is bonded to the solid surface via anionic groups of the surface reacted with ammonium groups thereof, and which is also linked via groups reactive with amino groups of the polyethylene imine of hydrophilic nonionic polymer in an amount of at least 50% by weight of the polyethylene imine.

The surprisingly high biopolymer-repellent effect is believed to be due to the fact that it is difficult to bond hydrophilic polymer in a closely-packed arrangement to a surface, since the individual hydrophilic polymer molecules repel each other.

Biopolymer repellency is obtained when polyethylene imine is reacted with hydrophilic polymer in solution. However, by first producing a polyethylene imine compound with hydrophilic polymer groups or side chains and then adsorbing this graft copolymer on the negatively charged solid surface, the hydrophilic polymer side chains are forced over the water side. The density and the thickness of the hydrophilic layer formed by the hydrophilic polymer chains is increased considerably, as compared to the prior art. Using the method of the invention, the hydrophilic polymer side chains are more closely packed on the surface than is advantageous with respect to the interaction between the repelling hydrophilic polymer chains. However, this interaction is counterbalanced, since the energy contribution due to the electrostatic attraction between the polyethylene imine and the surface is stronger than that due to the repellency between the hydrophilic polymer chains when these are compelled to pack themselves more closely.

The polyethylene imine with the hydrophilic polymer side chains has a polyethylene imine skeleton with a molecular weight within the range from about 10,000 to about 1,000,000, preferably from about 50,000 to about 500,000, containing secondary amino groups $-C_2H_4NH-$, as well as tertiary amino groups $-C_2H_4N$ and primary amino groups $-C_2H_4NH_2$, of which preferably less than 20% of the reactive hydrogens of the primary and secondary amino groups are substituted by hydrophilic polymer side chains, and optionally other substituents, such as alkyl groups, hydroxyl groups, hydroxyalkyl groups, amide groups, and functional groups utilized for grafting on the hydrophilic polymer side chains.

Reference herein to reaction with the polyethylene imine will accordingly be understood to include reaction with any or all of the types of amino groups present in the imine.

The hydrophilic polymer chains are nonionic polymers, such as polyethylene glycol, or randomly distributed or block-distributed polyalkylene glycols of ethylene oxide and alkylene oxides having from 3 to 4 carbon atoms, or tetrahydrofuran. Other suitable polymers are adducts of ethylene oxide, optionally in combination with higher alkylene oxides or tetrahydrofuran, with a dihydroxy or polyhydroxy compound, such as glycerol and pentaerythritol. Polysaccharides, such as dextran and starch; cellulose ethers, such as methyl cellulose, methyl hydroxypropyl cellulose, or ethyl hydroxyethyl cellulose; and polyvinyl alcohol are other suitable hydrophilic polymers. The hydrophilic polymer chains are water-soluble, and their molecular weight is within the range from about 400 to about 200,000, preferably from about 1,000 to about 100,000.

In the process according to the invention, the polyethylene imine with grafted hydrophilic polymer side chains is prepared by reacting the polyethylene imine with a hydrophilic polymer in an aqueous solution thereof. The ratio of reactive amino groups in the polyethylene imine to reactive end groups in the hydrophilic polymer is preferably adjusted such that the hydrophilic polymer is preferentially bonded at one end only. Examples of reactive end groups in the hydrophilic polymers are epoxide, aldehyde, sulphonic acid ester, such as tresylate, mesylate and tosylate, cyanuric chloride, carbonyl imidazole and active carboxylic acid ester groups. After reaction between the hydrophilic polymer and the polyethylene imine, remaining reactive groups at the ends of the hydrophilic polymer chains can be removed by reaction with, for example, 2-mercaptoethanol and 2-aminoethanol.

A different way of attaching hydrophilic polymer side chains to the polyethylene imine is to provide the latter with reactive groups capable of reacting with hydroxyl groups of the hydrophilic polymer.

Another alternative way of attaching hydrophilic polymer side chains to the polyethylene imine is to add ethylene oxide to the latter, optionally in combination with propylene or butylene oxide or tetrahydrofuran.

The resulting water-soluble polyethylene imine with hydrophilic polymer side chains is then adsorbed on a negatively charged solid surface. Examples of suitable surfaces are those which have a natural negative net charge, such as silica and glass, or those in which the negative charges have been generated by chemical or physical means. Negative charges can be induced on organic polymer surfaces, for example by acidic etching, i.e. a treatment with potassium permanganate in concentrated sulphuric acid, or by plasma- or radiation-induced grafting of, for example, acrylic acid or methacrylic acid. Examples of organic polymers suitable for this purpose are polystyrene, polyvinyl chloride, polyethylene, polymethyl methacrylate, polycarbonate, polysulfone and cellulose acetate.

The following Examples represent preferred embodiments of the invention.

EXAMPLE 1

A polystyrene plate having the dimensions 2 cm × 1 cm was washed in 70% ethanol for 3 minutes in an ultrasonic bath. The surface of the sample was air-dried and then oxidised for 30 seconds in $KMnO_4/H_2SO_4$, so that carboxylic acid and sulphonic acid groups were formed. The polystyrene plate was thoroughly rinsed in water. 5 g of a polyethylene glycol diepoxide of molecular weight 4,000 was dissolved in 45 ml aqueous sodium carbonate buffer at pH 9.5, and 0.43 g polyethylene imine (Polymin SN) of molecular weight 500,000 was added. The mixture was reacted for 3 hours at 45° C. with stirring. The polystyrene plate thus treated was placed in the solution containing the polyethylene imine derivative, which was adsorbed on the oxidised polystyrene surface for 2 hours at 40° C.

For comparison, as a Control, a polystyrene plate activated in the above manner was coated with the polyethylene imine from a 10% solution for 2 hours at 40° C. and pH 9.5. The resulting polyethylene imine-coated polystyrene surface was then repeatedly rinsed with water, and reacted with a 10% solution of the polyethylene glycol-diepoxide for 20 hours at 40° C. and pH 9.5.

The thickness of the nonionic hydrophilic layer was evaluated by ellipsometry, the dimensions of both the polyethylene glycolpolyethylene imine layer and of the polyethylene imine layer alone being determined. The thickness of the polyethylene glycol layer was obtained by substracting the latter value from the former.

The hydrophilisation effect was evaluated also by protein adsorption measurements by the ELISA technique. The amount of adsorbed protein is proportional to the absorbency at 490 nm.

TABLE I

| Product | OD 495 nm | Layer thickness (nm) | Weight ratio PEG/PEI, % |
|---|---|---|---|
| Untreated polystyrene | 1.254 | — | — |
| Polystyrene hydrophilised according to the invention | 0.107 | 42 | 87 |
| Polystyrene hydrophilised according to the Control | 0.500 | 1.6 | 13 |

PEG = polyethylene glycol
PEI = polyethylene imine

The above results show that the polyethylene glycol layer on the surface treated according to the invention has a far greater apparent thickness, and thus reaches far into the aqueous phase, whereas only a thin layer, in which the chains presumably are lying against the solid surface, is formed on the comparison product. The Table also shows that the hydrophilised surface according to the invention has a far higher protein repellency than the comparison product.

EXAMPLE 2

Pieces of low density polyethylene, polyvinyl chloride and polystyrene were cleaned in 70% ethanol and sulphated with $KMnO_4/H_2SO_4$ according to Example 1. A branched polyethylene glycol was produced by adding 320 mol ethylene oxide to di-trimethylol propane, and made reactive by reaction with cyanuric chloride. 5 g of the resulting product was dissolved in 45 ml aqueous sodium carbonate buffer (pH 9.5). Polyethylene imine 0.12 g was added, and the mixture was reacted for 3 hours at 45° C. Then the resulting polyethylene imine adduct was reacted with the activated polymer surfaces for 2 hours at 40° C., whereupon the surfaces were thoroughly rinsed with deionised water.

For comparison, as a Control, a hydrophilised product was produced by adsorbing polyethylene imine in the form of a 5% solution in aqueous sodium carbonate buffer (pH 9.5) to the activated polymer surfaces for 10 min., whereupon the above-mentioned branched polyethylene glycol derivative was reacted with the aminofunctional surfaces in the form of a 10% solution for 5 hours at 40° C. Finally, the pieces were thoroughly rinsed with deionised water. The test pieces were evaluated with ESCA, and the following results were obtained.

TABLE II

| Product | O/C | N/C | C-O/C-C | Weight ratio PEG/PEI, % |
|---|---|---|---|---|
| LD-PE according to the invention | 0.43 | 0.04 | 3.92 | 85 |
| LD-PE according to the comparison | 0.34 | 0.06 | 2.43 | 12 |
| PVC according to the invention | 0.38 | 0.07 | 3.82 | 78 |
| PVC according to the comparison | 0.29 | 0.11 | 1.71 | 10 |
| PS according to the invention | 0.41 | 0.06 | 3.55 | 90 |
| PS according to the comparison | 0.34 | 0.15 | 1.55 | 16 |

PEG = polyethylene glycol
PEI = polyethylene imine

It appears from the Table that the products according to the invention have a far denser grafting of polyethylene glycol chains than the product produced according to prior art technique. Especially interesting are the values in the column C-O/C-C which indicate the ratios between the carbon atoms in the polyethylene glycol chain and the carbon atoms in the respective LD-PE, PVC and PS surfaces. A higher value thus indicates a better surface coverage.

EXAMPLE 3

Pieces of polyethylene (PE) and polyvinyl chloride (PVC) were washed in 70% ethanol and grafted with crotonic acid under radiation with UV light of wavelength 350 nm in the presence of benzophenone as initiator for the introduction of carboxyl groups. A 10% solution of polyethylene glycol-bis(carbonyl imidazole) of molecular weight 4,000 was allowed to react with 0.24% polyethylene imine at pH 8.0 for 3 hours. The carboxyl-functional pieces were treated with the polyethylene imine derivative for 2 hours at 40° C., the derivatives being adsorbed onto the surfaces.

For comparison, as a Control, test surfaces of polyethylene and polyvinyl chloride were prepared. The activated surfaces were allowed to react with polyethylene imine in the form of a 10% solution for 2 hours at 40° C. and pH 9.5. The surfaces were repeatedly rinsed with water and reacted with a 9% solution of polyethylene glycol bis(carbonyl imidazole) of molecular weight 4,000 for 8 hours at 40° C. and pH 8.0. The hydrophilisation effect was evaluated by protein adsorption measurements according to the ELISA technique. The results were as follows.

TABLE III

| Product | OD 490 nm | Weight ratio PEG/PEI, % |
|---|---|---|
| PE according to the invention | 0.057 | 81 |
| PE according to the Control | 0.312 | 11 |
| PVC according to the invention | 0.3 | 71 |
| PVC according to the Control | 1.005 | 9 |

PEG = polyethylene glycol
PEI = polyethylene imine

The above results show a far better protein repellency when the hydrophilisation was carried out according to the invention.

EXAMPLE 4

A polystyrene plate having the dimensions 6 cm×1 cm was activated with $KMnO_4/H_2SO_4$, as described in Example 1. A 2% aqueous solution of the nonionic polysaccharide ethyl hydroxyethyl cellulose was treated with 0.3M $NaIO_4$ for 2 hours at 20° C., aldehyde groups being generated on the polysaccharide. To 50 ml of the polysaccharide solution, 0.4 g of a 30% solution of polyethylene imine of molecular weight 500,000, and 0.2 g sodium cyanoborohydride were added. After reaction for 2 hours at 20° C. and pH 7.0, the activated polystyrene surface was placed in the solution, the pH was raised to 9.5, and the bonding reaction allowed to proceed for 2 hours at 40° C.

The thickness of the nonionic hydrophilic layer as well as the protein adsorption were evaluated as in Example 1. The Table below clearly indicates that the polysaccharide layer on the surface hydrophilised in accordance with the invention reaches far into the solution and provides a highly effective protein repellency.

TABLE IV

| Product | Layer thickness (nm) | OD 495 nm | Weight ratio PEG/PEI, % |
|---|---|---|---|
| Untreated polystyrene | — | 1.390 | — |
| Polystyrene hydrophilised according to the invention | 23 | 0.095 | 180% |

EHEC = ethyl hydroxyethyl cellulose
PEI = polyethyl imine

Having regard to the foregoing disclosure, the following is claimed as the inventive and patentable embodiments thereof:

1. A process for preparing biopolymer-repellent solid surfaces having low spontaneous adsorption of proteins and other biopolymers through electrostatic attraction and/or hydrophobic interaction and useful in biochemical applications, comprising reacting a solid surface having anionic groups capable of reacting with ammonium groups, with a polyethylene imine substituted at least in part by at least 50% by weight of nonionic hydrophilic polymer thereby linking the polyethylene imine/hydrophilic polymer to the surface via anionic groups thereof, and forming a hydrophilic outer surface layer repellent to biopolymer and having low spontaneous adsorption of proteins and other biopolymers through electrostatic attraction and/or hydrophobic interaction.

2. A process according to claim 1 in which the nonionic hydrophilic polymer side chains are at least partly hydrophilic polyalkylene glycol chains deriving from at least one of ethylene oxide, propylene oxide, butylene oxide, and tetrahydrofuran.

3. A process according to claim 1 in which the nonionic hydrophilic polymer side chains are derived from water-soluble nonionic cellulose ethers.

4. A process according to claim 1 in which the solid surface is selected from polystyrene, polyvinyl chloride and polyethylene.

5. A biopolymer-repellent solid surface useful in biochemical applications, and having low spontaneous adsorption of proteins and other biopolymers through electrostatic attraction and/or hydrophobic interaction, the solid surface having a hydrophilic outer surface layer comprising polyethylene imine which is bonded to the solid surface via anionic groups of the surface reacted with ammonium groups thereof, and which is also linked via groups reactive with amino groups of the polyethylene imine to hydrophilic nonionic polymer in an amount of at least 50% by weight of the polyethylene imine.

6. A biopolymer-repellent solid surface according to claim 5 in which the hydrophilic nonionic polymer comprises chains of polyalkylene glycol from at least one of ethylene oxide, polypropylene oxide, butylene oxide, and tetrahydrofuran, distributed randomly or in blocks.

7. A biopolymer-repellent solid surface according to claim 5 in which the solid surface is selected from polystyrene, polyvinyl chloride, and polyethylene.

* * * * *